(12) United States Patent
Bascharon

(10) Patent No.: US 9,585,925 B1
(45) Date of Patent: Mar. 7, 2017

(54) PET FOOD SUPPLEMENT

(71) Applicant: Jamy A. Bascharon, Lisle, IL (US)

(72) Inventor: Jamy A. Bascharon, Lisle, IL (US)

(73) Assignee: Vetnique Labs LLC, Naperville, IL (US)

( * ) Notice: Subject to any disclaimer, the term of this patent is extended or adjusted under 35 U.S.C. 154(b) by 0 days.

(21) Appl. No.: 13/833,837

(22) Filed: Mar. 15, 2013

Related U.S. Application Data

(60) Provisional application No. 61/642,895, filed on May 4, 2012.

(51) Int. Cl.
| | | |
|---|---|---|
| A61K 36/42 | (2006.01) | |
| A61K 35/744 | (2015.01) | |
| A61K 31/353 | (2006.01) | |
| A61K 35/747 | (2015.01) | |

(52) U.S. Cl.
CPC ............ *A61K 36/42* (2013.01); *A61K 31/353* (2013.01); *A61K 35/744* (2013.01); *A61K 35/747* (2013.01)

(58) Field of Classification Search
CPC ...... A01N 25/006; A01N 63/04; C12R 1/645; C12R 1/885; C12N 1/14
USPC .............. 424/93.5, 639, 744, 495.1; 435/101
See application file for complete search history.

(56) References Cited

U.S. PATENT DOCUMENTS

| | | | | |
|---|---|---|---|---|
| 4,447,412 | A * | 5/1984 | Bilton | 424/498 |
| 4,755,504 | A * | 7/1988 | Liu | 514/26 |
| 6,203,797 | B1 * | 3/2001 | Perry | 424/93.45 |
| 6,900,173 | B2 * | 5/2005 | Martin et al. | 514/1 |
| 2005/0180962 | A1 * | 8/2005 | Raz et al. | 424/93.45 |
| 2010/0233312 | A9 * | 9/2010 | Stojanovic | A23K 1/004 426/2 |

OTHER PUBLICATIONS

MedLine Plus (Wayback Machine, Dec. 2010). Soluble vs. Insoluble Fiber.*
Wach et al. (2007). Quercetin content in some food and herbal samples. Food Chemistry, v100, p. 699-704.*
Jamie et al. (2002). Structural Carbohydrate Differences and Potential Dietary Fiber of Onion (*Allium cepa* L.) Tissues. J. Agric. Food Chem., v50, p. 122-128.*
Kubota et al. (2008). Biofilm Formation by Lactic Acid Bacteria and Resistance to Environmental Stress. Journal of Bioscience and Bioengineering, v106(4), p. 381-386.*
Jung et al. (2007). Anti-asthmatic Action of Quercetin and Rutin in Conscious Guinea-pigs Challenged with Aerosolized Ovalbumin. Arch Pharm Res, v30(12), p. 1599-1607.*
Morris et al. (1981). Nutritional Content of Selected Aboriginal Foods in Northeastern Colorado: Buffalo (Bison Bison) and Wild Onions (*Allium* Spp.). J. Ethnobiol., v1(2), p. 213-220.*
Liévin-Le Moal et al. (2002). Lactobacillus acidophilus (strain LB) from the resident adult human gastrointestinal microflora exerts activity against brush border damage promoted by a diarrhoeagenic *Escherichia coli* in human enterocyte-like cells. Gut, v50, p. 803-811.*
Swanson et al. (2001). Fructooligosaccharides and Lactobacillus acidophilus Modify Gut Microbial Populations, Total Tract Nutrient Digestibilities and Fecal Protein Catabolite Concentrations in Healthy Adult Dogs. The Journal of Nutrition, v132, p. 3721-3731.*
Gibson et al. (1994). Dietary Modulation of the Human Colonie Microbiota: Introducing the Concept of Prebiotics. The Journal of Nutrition, v125, p. 1401-1412.*
Lans et al. (2007). Ethnoveterinary medicines used to treat endoparasites and stomach problems in pigs and pets in British Columbia, Canada. Veterinary Parasitology, v148, p. 325-340.*
Glew et al. (2006). Amino Acid, Mineral and Fatty Acid Content of Pumpkin Seeds (*Cucurbita* spp) and *Cyperus esculentus* Nuts in the Republic of Niger. Plant Foods for Human Nutrition, v61, p. 51-56.*
Borelli et al. (2009). Fatal Onion (Allium Cepa) Toxicosis in Water Buffalo (Bubalus Bubalis). Journal of Veterinary Diagnostic Investigation, p. 21, p. 402-405.*
Anderson et al. (1988). Dietary fiber content of selected foods. The American Journal of Clinical Nutrition, v47, p.440-447.*
Maurer (2001). Bromelain: biochemistry, pharmacology and medical use. Cell. Mol. Life Sci., v58, p. 1234-1245.*
Weese et al. (2004). Oxalate degradation by intestinal lactic acid bacteria in dogs and cats. Veterinary Microbiology, v101, p. 161-166.*
Kovalkovičová et al. (2009). Some food toxic for pets. Interdisc Toxicol, v2(3), p. 169-176.*
Resnick et al. (2010). Nutritional Protocol for the Treatment of Intestinal Permeability Defects and Related Conditions. Natural Medicine Journal, v2(3), 16 pages.*
Yadav et al. Effect of supplementation of micronutrients and phytochemicals to fructooligosaccharides on growth response of probiotics and *E. coli*. Biofactors (Jan./Feb. 2011), v37(1), p. 58-64.*
No Scoot Powder, product desription http://www.naturvet.com/index.php?page=shop.product_details&flypage=flypage_images.tpl&category_id=15&product_id=159&option=com_virtuemart&Itemid=8.
Scoot bars, product insert http://www.petnaturals.com/sellsheets/SCOOTBARS.pdf.

\* cited by examiner

*Primary Examiner* — Scott Long
*Assistant Examiner* — Sean C Barron
(74) *Attorney, Agent, or Firm* — McDonnell Boehnen; Hulbert & Berghoff LLP

(57) ABSTRACT

This disclosure relates to methods of treating anal gland disease in subjects. In particular, the disclosure provides supplement compositions useful for treatment of anal gland disease. Such compositions comprise a probiotic, a fiber source, and an anti-inflammatory agent.

22 Claims, No Drawings

PET FOOD SUPPLEMENT

CROSS-REFERENCE TO RELATED APPLICATIONS

This application claims the benefit of the filing date of U.S. Provisional Patent Application Ser. No. 61/642,895, filed May 4, 2012, which is hereby incorporated by reference in its entirety.

BACKGROUND OF THE INVENTION

Field of the Invention

This disclosure relates to methods of treating anal gland disease in mammals. In particular, the disclosure provides supplement compositions useful for treatment of anal gland disease.

Description of Related Art

The anal glands (or anal sacs) are small glands found near the anus in many mammals, including pets such as dogs and cats. The two glands are located on either side of the anus, between the external and internal sphincter muscles. These glands secrete an oily discharge when the mammal defecates and this secretion is used for scent marking purposes. As the mammal defecates, the movement of the stool causes pressure over the glands, which secrete a few drops of liquid.

Many factors can cause the anal glands to not empty properly or to become inflamed and irritated, which can lead to various problems for the mammal. Some factors include poor quality stool (too soft or too small to exert pressure on the glands), allergies that may cause inflammation to the glands or the ducts where the liquid is secreted from, infection, and poor anatomy. When the glands do not empty regularly, the pressure builds up within the glands causing discomfort. If this continues an infection may set in and, if left unchecked, an abscess may develop which usually requires surgical treatment. Dogs or cats with severe ongoing anal gland problems may require complete surgical removal of the anal glands by a veterinarian.

The symptoms that a dog or cat with anal gland disease may display are: scooting the rear end on the ground, licking or biting at the rear, straining to defecate, giving away a very foul odor, defecating outside the litter box, etc. In severe cases, the sacs may abscess and rupture. Treatment usually involves having the glands manually emptied at a veterinarian's office or groomer. The standard recommendation for long-term treatment or prevention for animals that have repeated problems with their glands is a high fiber diet, which can help to add bulk and firm the stools.

The method by which fiber bulks up the stool is directly correlated to the ability of fiber to bind water in the large intestine. Feces are comprised of 75% water and 25% dry weight. The dry weight is comprised of bacteria and residue from unfermented fiber and excreted compounds. The amount of feces excreted a day varies for any one animal over a period of time. Of dietary constituents, only dietary fiber increases fecal weight. Water is distributed in the colon in three ways: 1) free water which can be absorbed from the colon, 2) water that is incorporated into bacterial mass, and 3) water that is bound by fiber. Fecal weight is dictated by: the holding of water by the residual dietary fiber after fermentation, the bacterial mass, and, possibly, an added osmotic effect of products of bacterial fermentation on fecal mass. Insoluble dietary fiber is minimally fermented and binds water. When added to the diet, insoluble fiber increases fecal weight in a predictable linear manner and decreases intestinal transit time. The greater the water-holding capacity of the fiber the greater the effect on fecal weight and bulk. For most healthy animals, an increase in wet fecal mass, depending on the particle size of the fiber, is generally on the order of 3-5 g/g fiber.

SUMMARY OF THE INVENTION

A supplement composition that is to be given to a subject aids in treatment and prevention of anal gland disease. The specific combination of ingredients improves gastro-intestinal health and produces consistent, firm, and bulky stools, which helps in natural emptying of the glands. The specific combination of ingredients also works in reducing inflammation of the glands that can occur in situations of chronic anal gland problems, infection, and/or allergies.

Thus, in a broad aspect, the disclosure encompasses supplement compositions, and methods employing such compositions in the treatment of anal gland disease in subjects.

One aspect of the disclosure provides a composition comprising (1) a probiotic, a prebiotic, or both, (2) a fiber source, and (3) an anti-inflammatory agent.

Another aspect of the disclosure provides a composition comprising (1) two or more fiber sources, and (2) at least one additional agent selected from the group selected from a probiotic, a prebiotic, an anti-inflammatory agent, an anti-histamine, an antibiotic, and an anti-diarrhea agent.

Another aspect of the disclosure provides a method of treatment of anal gland disease, the method comprising administering to a subject in need of such treatment an effective amount of one or more compositions of the disclosure.

Another aspect of the disclosure provides a method of preventing anal gland disease, the method comprising administering to a subject in need of such treatment an effective amount of one or more compositions of the disclosure.

Another aspect of the disclosure provides a method of treatment or prevention of anal gland disease, the method comprising administering to a subject in need of such treatment an effective amount of one or more compositions comprising two or more fiber sources.

DETAILED DESCRIPTION OF THE INVENTION

In one embodiment, the disclosure provides a composition comprising (1) a probiotic, a prebiotic, or both, (2) a fiber source, and (3) an anti-inflammatory agent.

In one embodiment, the disclosure provides a composition comprising (1) a probiotic, (2) a fiber source, and (3) an anti-inflammatory agent. In another embodiment, the disclosure provides a composition comprising (1) a prebiotic, (2) a fiber source, and (3) an anti-inflammatory agent. Yet in anther embodiment, the disclosure provides a composition comprising (1) a probiotic and a prebiotic, (2) a fiber source, and (3) an anti-inflammatory agent.

In another embodiment, the disclosure provides a composition comprising (1) two or more fiber sources, and (2) at least one additional agent selected from the group selected from a probiotic, a prebiotic, an anti-inflammatory agent, an anti-histamine, an antibiotic, and an anti-diarrhea agent. In yet another embodiment, at least one additional agent is the anti-inflammatory agent. In another embodiment, at least one additional agent is the probiotic. In yet another embodiment, at least one additional agent is the antibiotic. In one embodiment, the additional agents are the anti-inflammatory and the probiotic.

The probiotic of the disclosure is a strain selected from the group consisting of *Bifidobacterium, Lactobacillus, Lactococcus, Saccharomyces, Streptococcus,* and a combination thereof. Thus, in one embodiment, the probiotic is selected from the group consisting of: *Bacillus coagulans, Bifidobacterium animalis, Bifidobacterium bifidum, Bifidobacterium breve, Bifidobacterium infantis, Bifidobacterium lactis, Bifidobacterium longum, Lactobacillus acidophilus, Lactobacillus brevis, Lactobacillus casei, Lactobacillus gasseri, Lactobacillus lacti, Lactobacillus paracasei, Lactobacillus johnsonii, Lactobacillus plantarum, Lactobacillus reuteri, Lactobacillus rhamnosus, Enterococcus faecium, Saccharomyces boulardii,* and a combination thereof.

In one embodiment, the composition comprises one probiotic or two or more of different probiotics.

In another embodiment, the disclosure provides a composition as described above, wherein the probiotic is *Bifidobacterium animalis, Bifidobacterium bifidum, Bifidobacterium breve, Bifidobacterium infantis, Bifidobacterium lactis, Bifidobacterium longum, Lactobacillus acidophilus, Lactobacillus casei, Lactobacillus paracasei, Lactobacillus johnsonii, Lactobacillus plantarum, Lactobacillus reuteri, Lactobacillus rhamnosus,* and a combination thereof. In yet another embodiment, the probiotic is *Bifidobacterium animalis, Bifidobacterium breve, Bifidobacterium bifidum, Bifidobacterium infantis, Bifidobacterium lactis, Bifidobacterium longum,* and a combination thereof.

In certain embodiments, the disclosure provides a composition as described above, wherein the probiotic is *Lactobacillus acidophilus, Lactobacillus brevis, Lactobacillus casei, Lactobacillus gasseri, Lactobacillus lacti, Lactobacillus paracasei, Lactobacillus johnsonii, Lactobacillus plantarum, Lactobacillus reuteri, Lactobacillus rhamnosus,* and a combination thereof.

In one example embodiment, the disclosure provides a composition as described above, wherein the probiotic is *Lactobacillus acidophilus.*

In certain example embodiments, the disclosure provides compositions as described above, wherein the probiotic is in the amount of about $1 \times 10^3$ to about $1 \times 10^{10}$ CFU (colony-forming unit). In other example embodiments, the probiotic is in the amount of about $1 \times 10^5$ to about $1 \times 10^8$ CFU. In other example embodiments, the probiotic is in the amount of about $1 \times 10^5$ to about $1 \times 10^7$ CFU. In other embodiments, the probiotic is in the amount of about $1 \times 10^6$.

The prebiotic of the disclosure is selected from the group consisting of inulin, lactulose, galacto-oligosaccharide, fructooligosaccharide, mannooligosaccharide, larch arabinogalactan, xylooligosaccharide, polydextrose, tagatose, and a combination thereof. In certain example embodiments, the disclosure provides compositions as described above, wherein the prebiotic is in the range of 25 mg to 3000 mg.

The disclosure provides a composition as described above, wherein the fiber source provides bulk and firms up stools. The fiber source generally includes, but is not limited to, cellulose, pectins, gums, chitin, chitosan, β-glucans, hemicelluloses, inulins, oligofructose, fructooligosaccharides, lignin, polydextrose, *psyllium,* resistant dextrins, dandelion root, and resistant starch.

Cellulose, a polysaccharide consisting of linear β-(1,4)-linked glucopyranoside units, is the main structural component of plant cell walls. Mammals lack digestive enzymes to cleave β-(1,4) linkages and thus cannot absorb glucose from cellulose. Powdered cellulose is a purified, mechanically disintegrated cellulose obtained as a pulp from wood or cotton and is added to food.

Pectins, which are found in the cell wall and intracellular tissues of many fruits and berries, consist of galacturonic acid units with rhamnose interspersed in a linear chain. Pectins frequently have side chains of neutral sugars, and the galactose units may be esterified with a methyl group, a feature that allows for its viscosity. While fruits and vegetables contain 5 to 10 percent naturally occurring pectin, pectins are industrially extracted from citrus peels and apple pomace.

Gums consist of a diverse group of polysaccharides typically isolated from seeds. Guar gum is produced by the milling of the endosperm of the guar seed. The major polysaccharide in guar gum is galactomannan. Galactomannans are highly viscous and are therefore used for their thickening, gelling, and stabilizing properties.

Chitin is an amino-polysaccharide containing β-(1,4) linkages as is present in cellulose. Chitosan is the deacetylated product of chitin. Both chitin and chitosan are found in the exoskeletons of arthropods (e.g., crabs and lobsters) and in the cell walls of most fungi. Neither chitin nor chitosan is digested by mammalian digestive enzymes.

β-Glucans are homopolysaccharides of branched glucose resides. These β-linked D-glucopyranose polymers are constituents of fungi, algae, and higher plants (e.g., barley and oats).

Hemicelluloses are groups of polysaccharides found in plant cell walls that surround cellulose. These polymers can be linear or branched and consist of glucose, arabinose, mannose, xylose, and galacturonic acid.

Inulin and oligofructose are naturally occurring in a variety of plants. Most of the commercially available inulin and oligofructose is either synthesized from sucrose or extracted and purified from chicory roots. Oligofructose is also formed by partial hydrolysis of inulin. Inulin is a polydisperse β-(2,1)-linked fructan with a glucose molecule at the end of each fructose chain. The chain length is usually 2 to 60 units, with an average degree of polymerization. The β-(2,1) linkage is resistant to enzymatic digestion. Synthetic oligofructose contains β-(2,1) fructose chains with and without terminal glucose units. The chain ranges from two to eight monosaccharide residues.

Synthetic fructooligosaccharides have the same chemical and structural composition as oligofructose, except that the degree of polymerization ranges from two to four. The examples of naturally occurring fructans that are found in plants, include chicory, onions, and Jerusalem artichoke.

Lignin is a highly branched polymer comprised of phenylpropanoid units and is found within "woody" plant cell walls, covalently bound to fibrous polysaccharides.

Polydextrose is a polysaccharide that is synthesized by random polymerization of glucose and sorbitol. Polydextrose serves as a bulking agent in foods and sometimes as a sugar substitute. Polydextrose is not digested or absorbed in the small intestine and is partially fermented in the large intestine, with the remaining excreted in the feces.

*Psyllium* refers to the husk of *psyllium* seeds and is a very viscous mucilage in aqueous solution. The *psyllium* seed, also known as *plantago* or flea seed, is small, dark, reddish-brown, odorless, and nearly tasteless. *P. ovata,* known as blond or Indian *plantago* seed, is the species from which husk is usually derived. *P. ramosa* is known as Spanish or French *psyllium* seed.

Indigestible components of starch hydrolysates, as a result of heat and enzymatic treatment, yield indigestible dextrins that are also called resistant maltodextrins. Unlike gums, which have a high viscosity that can lead to problems in food processing and unpleasant organoleptic properties, resistant maltodextrins are easily added to foods and have a good mouth feel. Resistant maltodextrins are produced by heat and/or acid treatment of cornstarch, followed by enzymatic (amylase) treatment. The average molecular weight of resistant maltodextrins is 2,000 daltons and consists of polymers of glucose containing α-(1-4) and α-(1-6) glucosidic bonds, as well as 1-2 and 1-3 linkages. Resistant starch is naturally occurring, but can also be produced by the modification of starch during the processing of foods. Chemically modified starch includes starch esters, starch ethers, and cross-bonded starches that have been produced by the chemical modification of starch.

Thus, in one example embodiment, the composition as described above comprises one fiber source or two or more of different fiber sources.

In one example embodiment, the disclosure provides a composition as described above, wherein the fiber source is selected from the group consisting of barley, flax seed, digestion resistant maltodextrin, beet pulp, guar gum, inulin, cellulose, larch arabinogalactan, methylcellulose, oat bran, oligofructose, pectin, pumpkin powder, pumpkin seed, *psyllium*, rice bran, wheat bran, wheat dextrin, and a combination thereof.

In certain example embodiments, the disclosure provides a composition as described above, the fiber source is the fiber source is pectin, pumpkin powder, pumpkin seed, or a combination thereof.

In certain example embodiments, the disclosure provides compositions as described above, wherein the fiber source is in the amount of about 5% to about 90% weight of the composition (wt %). In other example embodiments, the fiber source is in the amount of about 5 to about 70 wt %. In another example embodiment, the fiber source is in the amount of about 10 to about 50 wt %. In yet another example embodiment, the fiber source is in the amount of about 15 to about 45 wt %. In other example embodiments, the fiber source is in the amount of about 20 to about 40 wt %. The fiber source is also in the amount of about 30 wt %.

The disclosure provides a composition as described above, wherein the anti-inflammatory agent treats or prevents inflammation. The anti-inflammatory generally includes, but is not limited to, non-steroidal anti-inflammatory agents, secondary metabolites (such as flavonoids), herbal agents, eicosanoids, steroids, antioxidants, and the like.

In one example embodiment, the disclosure provides a composition as described above, wherein the anti-inflammatory agent is selected from the group consisting of fish oil, bioflavonoid, bromelain, Vitamin C, Vitamin E, L-glutathione, selenium, reservatol, papain, flax seed oil, curcumin, ginger, alpha lipoic acid, zinc, quercetin, and a combination thereof. Examples of bioflavonoids include, but are not limited to, quercetin, epicatechin, oligomeric proanthocyanidins, kaempferol, myricetin, fisetin, isorhamnetin, pachypodol, rhamnazin, luteolin, apigenin, tangeritin, hesperetin, naringenin, eriodictyol, homoeriodictyol, taxifolin, and dihydrokaempferol.

In one example embodiment, the composition as described above comprises one anti-inflammatory agent or two or more of different anti-inflammatory agents.

In another example embodiment, the disclosure provides a composition as described above, wherein the anti-inflammatory agent is bromelain, quercetin, or a combination thereof.

In yet another example embodiment, the disclosure provides a composition as described above, wherein the anti-inflammatory agent is in the amount of about 0.1% to about 20% weight of the composition (wt %). In other example embodiments, the anti-inflammatory is in the amount of about 0.5 to about 15 wt %. In another example embodiment, the anti-inflammatory agent is in the amount of about 1 to about 10 wt %. In yet another example embodiment, the anti-inflammatory agent is in the amount of about 2 to about 10 wt %. In other example embodiments, the anti-inflammatory agent is in the amount of about 3 to about 15 wt %. The anti-inflammatory agent is also in the amount of about 10 wt %. The anti-inflammatory agent is also in the amount of about 5 wt %.

Any composition as described above may further comprise one or more of vitamins or minerals. Exemplary vitamins suitable for the composition of the disclosure include, but are not limited to, Vitamin A, Vitamin B1, Vitamin B2, Vitamin B3, Vitamin B5, Vitamin B6, Vitamin B7, Vitamin B9, Vitamin B12, Vitamin C, Vitamin D, Vitamin E, and Vitamin K. Exemplary minerals suitable for the composition of the disclosure include, but are not limited to, Potassium, Chlorine, Sodium, Calcium, Phosphorous, Magnesium, Zinc, Iron, Manganese, Copper, Iodine, Selenium, and Molybdenum.

In one example embodiment, the composition as described above comprises Vitamin A, Vitamin C, Vitamin D, Vitamin E, Zinc, Iron, and Selenium.

Any composition as described above may further comprise one or more of natural immune enhancers. Exemplary natural immune enhancers suitable for the composition of the disclosure include, but are not limited to, larch tree extract (Arabinogalactan), *Echinacea* plant extract, Elderberry, lysine, Lactoferrin, and *Olea* Europa Leaf.

In one example embodiment, the composition as described above comprises larch tree extract, *Echinacea* plant extract, and lysine.

Any composition as described above may further comprise one or more of anti-histamine agents.

Anti-histamine agents include, but are not limited to, azelastine, brompheniramine, buclizine, bromodiphenhydramine, carbinoxamine, cetirizine, cyclizine, chlorpheniramine, chlorodiphenhydramine, clemastine, cyproheptadine, desloratadine, dexbrompheniramine, deschlorpheniramine, dexchlorpheniramine, dimenhydrinate, dimetindene, diphenhydramine, doxylamine, ebastine, embramine, fexofenadine, levocetirizine, loratadine, meclozine, olopatadine, orphenadrine, phenindamine, pheniramine, phenyltoloxamine, promethazine, pyrilamine, quetiapine, rupatadine, tripelennamine, hydroxyzine, and a combination thereof.

In one example embodiment, the composition as described above comprises diphenhydramine, chlorpheniramine, clemastine, hydroxyzine, and a combination thereof.

Any composition as described above may further comprise one or more of antibiotics.

Examples of suitable antibiotics include, without limitation, amikacin, amoxicillin, amoxicilin-clavulanate, ampicillin, azithromycin, cefazolin, cefovecin, cefoxitin, cefpodoxime, ceftazidime, ceftiofur, cephalexin, chloramphenicol, ciprofloxacin, clindamycin, doxycylcine, enrofloxacin, gentamicin, imipenem, marbofloxacin, meropenem, metronidazole, orbifloxacin, penicillin, potentiated-sulfas, tetracycline, ticarcillin, tylosin, and a combination thereof.

In one example embodiment, the composition as described above comprises amoxicillin, amoxicilin-clavulanate, cephalexin, enrofloxacin, metronidazole, tylosin, and a combination thereof.

Any composition as described above may further comprise one or more of anti-diarrhea agents.

Anti-diarrhea agents include, but are not limited to, kaolinite, pectin, loperamide, atropine, diphenoxylate, bismuth subsalicylate, and a combination thereof.

In one example embodiment, the composition as described above comprises kaolinite/pectin, loperamide, diphenoxylate/atropine, and a combination thereof.

Any composition as described above may further comprise one or more of ingredients for improvement of flavor or palatability. Such ingredients may improve color, texture, taste, and smell. For example, the ingredients for improvement of flavor are made out of or resemble beef, pork, bacon, lamb, chicken, turkey, duck, liver, venison, fish (e.g., salmon and tuna), cheese, peanut butter, fruit, vegetable, and herb. The additional ingredients are in the amount of about 10% to about 90% weight of the composition (wt %). These agents can also be in the amount of about 20 to about 80 wt %, or about 30 to about 70 wt %, or about 40 to about 60 wt %.

In one embodiment, the composition of the disclosure comprises *L. Acidophilus*, pumpkin seed, quercetin, and bromelain.

In one embodiment, the composition of the disclosure comprises *L. Acidophilus*, pumpkin seed, quercetin, bromelain, and apple pectin.

In one embodiment, the composition of the disclosure comprises *L. Acidophilus*, pumpkin seed, quercetin, and bromelain, and kaolinite.

In one embodiment, the composition of the disclosure comprises *L. Acidophilus*, pumpkin seed, quercetin, and bromelain, apple pectin and kaolinite.

In another aspect, the present disclosure provides methods of treating or preventing anal gland disease, the method comprising administering to a subject in need of such treatment an effective amount of one or more of compositions of the disclosure. Any disclosed composition, or a combination of compositions may be used in these methods.

In yet another aspect, the present disclosure provides methods of treatment or prevention of anal gland disease, the method comprising administering to a subject in need of such treatment an effective amount of one or more compositions comprising two or more fiber sources. Suitable fiber sources as described above. In one embodiment of this method, the fiber source is pectin, pumpkin, pumpkin seed, or a combination thereof. In another embodiment of this method, the fiber source is pumpkin, pumpkin seed, or a combination thereof.

In one embodiment, the disclosure provides methods of treating anal gland disease. In another embodiment, the disclosure provides methods of preventing anal gland disease.

The disclosure provides methods as described above, wherein the subject is a pet. In one embodiment, the subject is a dog or a cat. In another embodiment, the subject is a dog. In other embodiment, the subject is a cat.

In one example embodiment, the administration is oral.

In certain example embodiments, in the methods as described above, the administration is in the form of a supplement. In some embodiments, the composition is administered as a supplement to the feed. For example, the compositions of the disclosure may be added to a subject's food during a regular feeding. In other example embodiments, the composition is administered without any food concurrently given to the subject. In some example embodiments, the compositions of the disclosure may be formulated into a pill. In other example embodiments, the compositions of the disclosure above may be formulated as a powder, tablet, caplet, capsule, or suspension. In other example embodiments, the compositions of the disclosure may be formulated into a treat or integrated into a pet food.

In certain example embodiments, in the methods as described above, the administration is daily. In other example embodiments, in the methods as described above, the administration is once daily. In other example embodiments, in the methods as described above, the administration is two or three times per day. Daily administration may be over a continued, long-term period (e.g., from a few days to a few years).

In certain example embodiments, in the methods as described above, the administration is every other day, twice weekly, or three times weekly. Such administration may be over a continued, long-term period (e.g., from a few days to a few years).

In certain example embodiments, in the methods as described above, the administration is episodically, for example on an as needed basis when the subject is experiencing anal gland problems for a short-term period of several months.

In another aspect, the present disclosure provides compositions as described and an appropriate carrier, excipient or diluent. The exact nature of the carrier, excipient or diluent will depend upon the desired use for the composition, suitable or acceptable for any veterinary use. The composition may optionally include one or more additional compounds.

When used to treat or prevent such diseases, the compositions described herein may be administered singly, as mixtures of one or more compositions or in mixture or combination with other agents useful for treating or preventing such diseases and/or the symptoms associated with such diseases. The compounds may also be administered in mixture or in combination with agents useful to treat or prevent other disorders or maladies, such examples could include steroids, immunosuppressants, antacids, gastro-intestinal protectants, anthelmintics, reflux suppressants, laxatives, analgesics, as well as additional classes of drugs.

Compositions may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For oral administration, the compositions may take the form of, for example, powder, lozenges, tablets or capsules prepared by conventional means with acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films, or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, stabilizers, flavoring, coloring, and sweetening agents as appropriate.

Preparations for oral administration may be suitably formulated to give controlled release of the ingredients, as is well known.

Oral administration also includes supplements, medicines, nutritionally complete diets, veterinary prescription diets, as well as any type of usual food products, such as, for example, confectionery, pastries, milk-containing products, cereals, biscuits, pet treats, pet chews, pet bars, sugar-based and fat-based confectionery products, drinks, liquid compositions and the like.

The compositions described herein will generally be used in an amount effective to achieve the intended result, for example in an amount effective to treat or prevent the anal gland disease. By therapeutic benefit is meant eradication or amelioration of the anal gland disease and/or eradication or amelioration of one or more of the symptoms associated with the anal gland disease such that the subject shows an improvement in feeling or condition, notwithstanding that the subject may still be afflicted with the disease. Therapeutic benefit also generally includes halting or slowing the progression of the anal gland disease, regardless of whether improvement is realized.

The amount of compositions administered will depend upon a variety of factors, including, for example, the severity of the disease symptoms, the age and weight of the subject, etc. Determination of an effective dosage of compositions is within the capabilities of those skilled in the art.

DEFINITIONS

The following terms and expressions used herein have the indicated meanings.

The term "anti-inflammatory agent", as used herein, refers to any compound or mixture of compounds that treats or prevents inflammation.

The term "fiber" or "fiber source" or "dietary fiber", as used herein, refers to non-digestible carbohydrates and lignin that are intrinsic and intact in plants and have beneficial physiological effects in mammals. Total fiber contains two main components, soluble fiber that is readily fermented in the colon into gases and metabolically active byproducts (such as short-chain fatty acids), and insoluble fiber that is metabolically inert, absorbs water as it moves through the digestive system, and eases defecation. Unless otherwise specified, fiber includes dietary fiber and/or functional fiber.

The term "probiotic", as used herein, refers to live microorganisms, which when administered in adequate amounts confer a health benefit on the host. Probiotics are commonly consumed as part of fermented foods with specially added active live cultures; such as food supplements. When given to the subject, probiotics may improve the beneficial microflora of the gastro-intestinal tract.

"Treating" or "treatment" as used herein covers the treatment of a disease or disorder described herein, in a subject, preferably a pet, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, ameliorating, or slowing progression of one or more symptoms of the disease or disorder.

"Subject" refers to a warm blooded animal such as a mammal, for example a pet, or in another example a dog or a cat, which is afflicted with, or has the potential to be afflicted with the diseases and disorders described herein.

EXAMPLES

The methods of the disclosure are further illustrated by the following examples, which are not to be construed as limiting the disclosure in scope or spirit to the specific procedures and compositions described in them.

Example 1

A supplement composition is prepared by mixing the ingredients as solids (in powdered form) at room temperature. A composition is listed in Table 1. Compositions of different doses can be prepared by modifying the loading and the composition of the ingredients and total tablet weight.

TABLE 1

| INGREDIENT | ACTIVE | AMOUNT | % |
|---|---|---|---|
| Dessicated Beef Liver Powder | Active | 1,675 mg | 56.7% |
| Pumpkin Seed Powder | Active | 890 mg | 30.1% |
| Apple Pectin Cellulose Powder | Active | 135 mg | 4.6% |
| Quercetin Dihydrate | Active | 100 mg | 3.4% |
| Lactobacillus acidophilus (5 Billion CFU/gram) | Active | 96 mg | 3.2% |
| Bromelain | Active | 60 mg | 2.0% |
| TOTAL | | 2.956 g | 100% |

Example 2

A supplement composition is prepared by mixing the ingredients as solids, and this composition is listed in Table 2.

TABLE 2

| INGREDIENT | ACTIVE | AMOUNT | % |
|---|---|---|---|
| Dessicated Beef Liver Powder | Active | 1,666 mg | 50% |
| Quercetin Dihydrate | Active | 125 mg | 3.9% |
| Bromelain | Active | 62.5 mg | 1.9% |
| Kaolinite | Active | 500 mg | 15% |
| Apple Pectin Cellulose Powder | Active | 125 mg | 3.9% |
| PumpkinSeed Powder | Active | 825 mg | 25% |
| Lactobacillus acidophilus (5 billion CFU/gram) | Active | 10 mg | 0.3% |
| TOTAL | | 3.314 g | 100% |

Example 3

Additional supplements are shown in Tables 3-6.

TABLE 3

| INGREDIENT | ACTIVE | AMOUNT | % |
|---|---|---|---|
| Dessicated Beef Liver Powder | Active | 1,666 mg | 59% |
| Pumpkin Seed Powder | Active | 825 mg | 29% |
| Quercetin Dihydrate | Active | 125 mg | 4.6% |
| Apple Pectin Cellulose Powder | Active | 125 mg | 4.6% |
| Tylosin | Active | 62.5 mg | 2.3% |
| Lactobacillus acidophilus (5 billion CFU/gram) | Active | 10 mg | 0.5% |
| TOTAL | | 2.814 g | 100% |

TABLE 4

| INGREDIENT | ACTIVE | AMOUNT | % |
|---|---|---|---|
| Dessicated Beef Liver Powder | Active | 1,666 mg | 59% |
| Pumpkin Seed Powder | Active | 825 mg | 29% |
| Quercetin Dihydrate | Active | 125 mg | 4.6% |
| Apple Pectin Cellulose Powder | Active | 125 mg | 4.6% |
| Bromelain | Active | 62.5 mg | 2.3% |
| Enterococcus faecium (5 billion CFU/gram) | Active | 10 mg | 0.5% |
| TOTAL | | 2.814 g | 100% |

TABLE 5

| INGREDIENT | ACTIVE | AMOUNT | % |
|---|---|---|---|
| Dessicated Beef Liver Powder | Active | 1,666 mg | 50% |
| Quercetin Dihydrate | Active | 125 mg | 3.9% |
| Bromelain | Active | 62.5 mg | 1.9% |
| Wheat Bran | Active | 500 mg | 15% |
| Apple Pectin Cellulose Powder | Active | 125 mg | 3.9% |
| Pumpkin Seed Powder | Active | 825 mg | 25% |
| Lactobacillus acidophilus (5 billion CFU/gram) | Active | 10 mg | 0.3% |
| TOTAL | | 3.314 g | 100% |

TABLE 6

| INGREDIENT | ACTIVE | AMOUNT | % |
|---|---|---|---|
| Dessicated Beef Liver Powder | Active | 1,666 mg | 50% |
| Quercetin Dihydrate | Active | 125 mg | 3.9% |
| Bromelain | Active | 62.5 mg | 1.9% |
| Flax Seed | Active | 500 mg | 15% |
| Apple Pectin Cellulose Powder | Active | 125 mg | 3.9% |
| PumpkinSeed Powder | Active | 825 mg | 25% |
| Lactobacillus acidophilus (5 billion CFU/gram) | Active | 10 mg | 0.3% |
| TOTAL | | 3.314 g | 100% |

Example 4

The composition of Example 1 was administered as an additive to the pet food on a long-term basis. One ⅛ teaspoon of powder composition is added to the feed once daily for dogs and cats weighing about 1-15 lbs; one ¼ teaspoon of powder composition is added to the feed once daily for dogs and cats weighing about 16-25 lbs; ½ teaspoon of powder composition is added to the feed once daily for dogs weighing about 26-50 lbs; ¾ teaspoon of powder composition is added to the feed once daily for dogs weighing about 51-75 lbs, and 1 teaspoon of powder composition is added to the feed once daily for dogs 76 pounds or more.

Example 5

Additional supplements of the invention may be prepared are shown in Table 7.

TABLE 7

| INGREDIENT | ACTIVE | AMOUNT | % |
|---|---|---|---|
| Dessicated Beef Liver Powder | Active | 1675 mg | 47.2% |
| Fructo-Oligosaccharide | Active | 750 mg | 21.1% |
| Pumpkin Seed Powder | Active | 890 mg | 25.1% |
| Apple Pectin Cellulose Powder | Active | 135 mg | 3.8% |
| Quercetin | Active | 100 mg | 2.8% |
| TOTAL | | 3.550 g | 100% |

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A composition comprising (1) a probiotic, a prebiotic, or both, (2) a fiber source, and (3) quercetin, where quercetin is present in the amount of about 3 weight % to about 5 weight %, and where the composition reduces inflammation of anal glands.

2. A composition according to claim 1 further comprising a digestive enzyme.

3. A composition according to claim 2, wherein the digestive enzyme is bromelain.

4. The composition according to claim 2, further comprising apple pectin.

5. A composition comprising (1) a probiotic, where the probiotic is present in the amount of about $1 \times 10^3$ to about $1 \times 10^{10}$ colony-forming units, (2) a fiber source, and (3) quercetin, where quercetin is present in the amount of about 3 weight % to about 5 weight %.

6. The composition according to claim 5, further comprising an anti-histamine agent.

7. The composition according to claim 5, further comprising one or more of vitamins, minerals, or a combination thereof.

8. The composition according to claim 5, comprising the probiotic that is a strain selected from the group consisting of Bifidobacterium, Lactobacillus, Lactococcus, Saccharomyces, Streptococcus, and a combination thereof.

9. The composition according to claim 8, wherein the probiotic is Lactobacillus acidophilus.

10. The composition according to claim 5, wherein the fiber source is selected from the group consisting of barley, flax seed, digestion resistant maltodextrin, beet pulp, guar gum, inulin, cellulose, larch arabinogalactan, methylcellulose, oat bran, oligofructose, pectin, pumpkin powder, pumpkin seed, *psyllium*, rice bran, wheat bran, wheat dextrin, and a combination thereof.

11. The composition according to claim 5, further comprising an agent for improvement of flavor.

12. The composition according to claim 5, which comprises: *L. Acidophilus*, pumpkin seed, and bromelain.

13. The composition according to claim 12, further comprising apple pectin.

14. A composition comprising (1) two or more fiber sources, (2) quercetin, where quercetin is present in the amount of about 3 weight % to about 5 weight %, and (3) at least one additional agent selected from the group selected from a probiotic, a prebiotic, an anti-inflammatory agent, and an anti-histamine.

15. The composition according to claim 14, wherein the fiber source is selected from the group consisting of barley, flax seed, digestion resistant maltodextrin, beet pulp, guar gum, inulin, cellulose, larch arabinogalactan, methylcellulose, oat bran, oligofructose, pectin, pumpkin powder, pumpkin seed, *psyllium*, rice bran, wheat bran, wheat dextrin, and a combination thereof.

16. The composition according to claim 14, comprising the probiotic, which is *Lactobacillus acidophilus*.

17. The composition according to claim 14, comprising the anti-inflammatory agent that is selected from the group consisting of fish oil, bromelain, Vitamin C, Vitamin E, L-glutathione, selenium, reservatol, papain, flax seed oil, curcumin, ginger, alpha lipoic acid, zinc, and a combination thereof.

18. A method of treatment or prevention of anal gland disease, the method comprising administering to a subject in need of such treatment an effective amount of one or more compositions according to claim 5.

19. The method according to claim 18, wherein the subject is a dog or a cat.

20. A method of treatment or prevention of anal gland disease, the method comprising administering to a subject in need of such treatment an effective amount of one or more compositions according to claim 14.

21. The method according to claim 20, wherein the subject is a dog or a cat.

22. The composition according to claim 14, wherein an anti-inflammatory agent is bioflavonoid selected from the group consisting of epicatechin, oligomeric proanthocyanidins, kaempferol, myricetin, fisetin, isorhamnetin, pachypodol, rhamnazin, luteolin, apigenin, tangeritin, hesperetin, naringenin, eriodictyol, homoeriodictyol, taxifolin, and dihydrokaempferol.

* * * * *